United States Patent
King et al.

(10) Patent No.: US 9,912,911 B2
(45) Date of Patent: Mar. 6, 2018

(54) INTER-MODULE LINK INTERFACE

(71) Applicant: Karl Storz Imaging, Inc., Goleta, CA (US)

(72) Inventors: Timothy King, Goleta, CA (US); Jason Radtke, Goleta, CA (US); Brendon Bolin, Goleta, CA (US); Tony Wonsyld, Goleta, CA (US)

(73) Assignee: Karl Storz Imaging, Inc., Goleta, CA (US)

( * ) Notice: Subject to any disclaimer, the term of this patent is extended or adjusted under 35 U.S.C. 154(b) by 417 days.

(21) Appl. No.: 13/731,167

(22) Filed: Dec. 31, 2012

(65) Prior Publication Data
US 2014/0184770 A1    Jul. 3, 2014

(51) Int. Cl.
*H04N 7/18* (2006.01)
*H04N 5/232* (2006.01)
*A61B 1/00* (2006.01)

(52) U.S. Cl.
CPC ........... *H04N 7/18* (2013.01); *A61B 1/00018* (2013.01); *A61B 1/00114* (2013.01); *H04N 5/23225* (2013.01); *A61B 1/00124* (2013.01); *F04C 2270/0421* (2013.01)

(58) Field of Classification Search
CPC ........... A61B 1/00018; A61B 1/00114; H04N 5/23225; H04N 7/18; H04N 5/38
See application file for complete search history.

(56) References Cited

U.S. PATENT DOCUMENTS

| | | | |
|---|---|---|---|
| 5,894,322 A * | 4/1999 | Hamano | A61B 1/00006 348/65 |
| 5,976,070 A | 11/1999 | Ono et al. | |
| 6,960,161 B2 | 11/2005 | Amling et al. | |
| 7,212,227 B2 | 5/2007 | Amling et al. | |
| 7,316,646 B2 | 1/2008 | Amling et al. | |
| 7,471,310 B2 | 12/2008 | Amling et al. | |
| 7,520,853 B2 | 4/2009 | Amling et al. | |
| 7,821,530 B2 | 10/2010 | Amling et al. | |
| 7,855,727 B2 | 12/2010 | Adler et al. | |
| 8,059,160 B2 | 11/2011 | Shinozaki et al. | |
| 8,089,509 B2 | 1/2012 | Chatenever et al. | |
| 8,199,188 B2 | 6/2012 | Amling et al. | |
| 8,274,559 B2 | 9/2012 | Amling et al. | |
| 2003/0097657 A1* | 5/2003 | Zhou | H04N 7/163 725/46 |
| 2004/0201686 A1* | 10/2004 | Amling | A61B 1/00059 348/207.1 |

(Continued)

OTHER PUBLICATIONS

European Search Report Application No. EP 13 19 8243 Completed: Jun. 18, 2014; dated Jun. 26, 2014 6 pages.

*Primary Examiner* — Md Haque
(74) *Attorney, Agent, or Firm* — Whitmyer IP Group LLC

(57) ABSTRACT

A multi-function cable, and more particularly, a multi-function cable having components permitting its interchangeable use with a variety of modules, the modules including endoscopes, cameras input units and display units. The multi-function cable is capable of receiving inputs from multiple different types of modules having diverse data and signal formats and may generate diverse output signals compatible with differing modules. The multi-function cable is used in a medical operating room.

31 Claims, 11 Drawing Sheets

(56) References Cited

U.S. PATENT DOCUMENTS

| | | | |
|---|---|---|---|
| 2005/0200698 A1* | 9/2005 | Amling | A61B 1/00059 |
| | | | 348/65 |
| 2007/0024717 A1* | 2/2007 | Chatenever | A61B 1/042 |
| | | | 348/211.99 |
| 2007/0088812 A1* | 4/2007 | Clark | H04L 12/2803 |
| | | | 709/223 |
| 2011/0029733 A1 | 2/2011 | Adler et al. | |
| 2012/0013755 A1 | 1/2012 | Shinozaki et al. | |
| 2013/0096382 A1* | 4/2013 | Alexander | A61B 1/00016 |
| | | | 600/110 |
| 2014/0184764 A1* | 7/2014 | Amling | A61B 1/00105 |
| | | | 348/65 |

* cited by examiner

INTER-MODULE LINK INTERFACE

FIELD OF THE INVENTION

The invention relates to a multi-function cable, and more particularly, a multi-function cable having components permitting its interchangeable use with a variety of modules, the modules including endoscopes, cameras, input modules, control modules and display modules. The multi-function cable is capable of transferring data and electrical signals from various types of input modules to various types of control modules that are connected to a display.

BACKGROUND OF THE INVENTION

The field of endoscopy, to which the present invention relates, includes medical diagnostic and therapeutic disciplines that utilize endoscopes to view otherwise inaccessible body cavities using minimally invasive surgical procedures. Endoscopes typically include cameras located at the distal tip of the endoscopes to capture images. Endoscopic cameras are typically small and lightweight for ease of use by medical professionals.

In known systems, endoscopic cameras are typically connected to a Camera Control Unit ("CCU"), with the CCU processing and displaying the imaging data transmitted from the endoscopic camera. Often, each medical procedure requires a different camera, leading to a large inventory of cameras. Additionally, each camera must be compatible with the CCU to function correctly. As such, each CCU has software to process and operate a variety of camera technologies, and as new technologies become available, the CCU may need updated software to properly process images from new camera technology. Additionally, the CCU hardware may become outdated, thus requiring an entirely new CCU to process the images of both old and new camera technologies used by a physician.

CCUs may be designed to be reprogrammable and reconfigurable, and as such, an older model CCU may sometimes be upgraded or configured to work with a new camera technology. However, in many cases the older model CCU may be too outdated to update or it may be less costly to replace the older module CCU with a new one because the reconfiguring of the CCU is often a time and labor intensive process that requires the CCU be returned to the manufacturer for disassembly, installation of new components and testing. Moreover, while it may be possible to update software in older model CCUs, the existing hardware in older model CCUs does not allow for the older model CCUs to support software for newer technology image sensors and image formats provided with newly developed camera technology.

In known systems, endoscopic cameras used during endoscopic surgery are typically referred to as heads or camera heads. To achieve the desired size and weight of the camera heads, camera head and/or integrated endoscope-camera assembly electronics are typically separated physically from the majority of circuitry required to process and output high-quality, color video images. The endoscope-camera assembly electronics is typically stored in the CCU. In known systems, CCUs may be placed on or in carts, or may be permanently wall-mounted.

In known video imaging systems, the interconnection between the CCUs and the camera heads is typically achieved by means of a cable. In known systems, usually one cable end is permanently fixed to the camera head, while the other cable end is detachably connected to the CCU using a connector, which may lock the end of the cable to the module. The cables of the known video imaging systems are small in diameter and lightweight, but rugged enough to withstand repeated sterilization, accidental gurney wheel "run-over," and the like.

In known video imaging systems, the cables simply connect a camera head to a CCU. When image data is acquired, or picked up, it is sent by the camera head to the CCU through the cable. Upon receiving the image data from the camera head, the CCU normally processes the signal and displays the acquired image on a viewing device. Generally, the image is used by a medical professional and/or for storage on various media (video cassette recorder, floppy disk, hard drives, flash drives, compact disks, digital video disks, and the like) and/or for transmission to remote locations in various manners, such as by the Intranet, Internet, radio transmission, and the like.

Additionally, the CCU may send commands to the camera head to adjust various settings (i.e. color balance, electronic shutter for light sensitivity, and other optical and electronic characteristics).

Traditionally, CCUs are compatible with a limited number of camera heads. A CCU's hardware is usually difficult to configure for proper communication with varying types of camera heads because camera heads use varying types of imaging devices that can differ in pixel resolution, timing requirements (i.e. PAL, NTSC, Progressive, and other formats), signal output type (i.e. analog or digital), physical size, and in other characteristics.

Analog video system types differ in scanning principles, resolution capability, sampling rates, aspect ratios, synchronization, bandwidth, and the like. Moreover, video system types may differ between broadcast, closed circuit, and computer applications. Analog video systems are typically classified as either composite (luminance and chrominance components multiplexed into a single signal) or component (separate signals for each chrominance component, and synchronization signals). In broadcasting applications, composite formats are generally used. For closed circuit systems (such as video production and editing, medical, industrial, and scientific applications) typically component formats are used. The primary composite analog video standards usually used are PAL, NTSC, and SECAM, with one specific standard used in different geographical areas.

Digital video systems are typically differentiated by their application. Advanced television (ATV), high definition television (HDTV), and computer systems may differ in format and signal characteristics. In some areas, digital video formats and standards are currently being developed and adopted. The Society of Motion Picture and Television Engineers (SMPTE) is typically in the business of defining and adopting voluminous digital video formal standards. As each is adopted, various applications, and application improvements generally will also be realized. Some digital video standards currently in use are: IEEE-1394 FireWire®, ISO/IEC IS 13818, International Standard (1994), MPEG-2, and ITU-R BT.601-4 (1994) Encoding Parameters of Digital Television for Studios.

Furthermore, there may be variability from device to device of the same type, which may affect camera head performance. Additionally, commands sent from the CCU to the camera head are generally unique depending upon the camera head type being used. Moreover, as repairs, modifications, or improvements are made to camera heads, the CCU, which was originally designed to be compatible with the older camera head, may become incompatible and may require upgrading as well.

This overall variability in camera heads, either caused by imaging device technologies or by CCU command characteristics, often results in a CCU being specifically designed to be compatible with the camera head type utilized. Also, consumers may desire different capabilities related to specific applications of the cameras, including medical, industrial, and scientific uses. Capabilities include picture to picture, reverse video, electronic zoom, still image capture, and stereoscopic video interface.

Moreover, CCUs are typically designed for use with camera head technologies currently in existence, and not designed to anticipate and accommodate camera heads yet to be developed. Hence, CCUs are typically not designed to be compatible with future camera head technologies; particularly, image device and image signal transmission technologies. These differences between older and newer camera heads also contribute to compatibility problems.

Although current CCU devices allow for upgradeability, each new camera head may include software required to update a CCU to be compatible with that (or an identical) camera head. Since many procedures require different cameras, the CCU must be properly maintained and updated to be compatible with each camera. Therefore, it is important to have an efficient way to manage software updating and reprogramming of camera heads and/or imaging devices.

Because CCUs are usually compatible with limited quantities of camera heads, CCUs are typically discarded in favor of ones that were designed concurrently and/or to be compatible with particular camera head technologies. Consequently, CCUs have become an added expense often associated with changing imaging devices or camera heads. Further, it is typically desired for camera heads to be improved due to the demand from consumers to have the latest technology and advancement in equipment. Moreover, CCUs used in medical and veterinary fields are increasingly being mounted permanently in equipment bays or carts and/or permanently mounted within the walls of surgical operating rooms themselves. The expense associated with replacing CCUs to maintain compatibility with camera heads is subsequently passed onto consumers.

Thus, there exists a need for a modular imaging system that overcomes the disadvantages of the prior art. There exists a need to provide a system having at least one modular input module that may be connected to various camera heads and that may receive data in various formats from various camera heads. There exists a need for the at least one modular input module to be connected to a control module that may be updated or reprogrammed in an efficient and cost effective manner, rather than replacing the older input module or control module with a newer module. There exists a need for the modular imaging system, including at least one input module and a control module, to be readily compatible with existing and future imaging technologies and that allows for the at least one input module and the control module to be backwards and forwards compatible.

Thus, it is desired to provide a modular imaging system that automatically reprograms the software in one module using the other modules' reprogrammable files upon attachment of the modules using a cable or data link. It is also desired to provide a modular imaging system including a cable that has forward and backward compatibility between older modules and newer modules upon connection to one another via the cable.

It is also desired to determine inter-module compatibility between modules at power-up and/or when hot-plugging the cable between modules that are already powered up. It is also desired to reprogram the software in one module with the other module to bring one module up to the compatibility of the other module upon connecting the modules via the cable.

It is also desired to configure and control features of one module from another module upon attachment of one module to another via the cable. It is also desired to control the power state of one module via the other module upon attachment of the modules via the cable.

SUMMARY OF THE INVENTION

Accordingly, it is an object of the invention to provide a cable that allows for connections to be made between two modules, such as an input module and a control module. The control module may be connected to a display such that the control module controls the display of images on the display.

It is another object of the invention to provide a modular imaging system including a system that automatically reprograms the software in a module upon execution of software on another module, once the modules are connected to one another via a cable. It is an object of the invention to reprogram one module using the other modules' reprogrammable files. It is another object of the invention to provide a modular imaging system including a cable for forward and backward compatibility between older modules and newer modules upon connection to one another via the cable.

It is another object of the invention to determine inter-module compatibility between modules at power-up and/or when hot-plugging the cable between modules that are already powered up. It is another object of the invention to reprogram the software in one module with the other module to bring one module up to the compatibility of the other module upon connecting the modules via the cable.

It is another object of the invention to configure and control features of one module from another module upon attachment of one module to another via the cable. It is another object of the invention to control the power state of one module via the other module upon coupling of the modules via the cable.

Accordingly, these and other objects of the invention are achieved by providing a cable for connecting an input module and a control module in a modular imaging system, the cable comprising: a first set of wires, the first set of wires allowing for video data to be transmitted across the cable; a second set of wires, the second set of wires allowing for image control data to be transmitted across the cable; a third set of wires, the third set of wires allowing for power control data to be transmitted across the cable; and pin connectors, the pin connectors being located on each end of the cable, such that each of the pin connectors corresponds to an individual electrical wire.

In certain embodiments, the cable further comprises a fourth set of wires, the fourth set of wires attached to the pin connectors, the fourth set of wires having an undefined function to allow for expansion of functionality across the cable.

In certain embodiments, the cable transfers digital video data across the first set of wires. In certain embodiments, the digital video data is sent in run-time programmable images sizes, color spaces, bit-depths and frame-rates.

In certain embodiments, the cable is double ended, such that either end of the cable is pluggable into the input module and the control module.

In certain embodiments, upon connection of the input module to the control module via the cable, software executes in the control module to transmit image control data through the second set of wires to determine if the software in the control module is compatible with the software in the input module.

In certain embodiments, the cable allows for image control data to be transmitted between the input module and the control module through the second set of wires to program software files in either the input module or the control module, so that the input module is compatible with the control module.

In certain embodiments, after the software files in either the input module or the control module are programmed, power is automatically cycled to the module whose software files have been programmed.

In certain embodiments, the cable allows for control of the input module from the control module and vice-versa through the second set of wires.

In certain embodiments, the cable allows for the input module to be electrically linked to the control module at power-up.

In certain embodiments, the cable allows for the input module to be linked to the control module when plugging the cable between the input module and the control module, and wherein the input module and the control module are already powered up.

In certain embodiments, the cable allows for controlling the power state of the input module from the control module and vice-versa through power control data transmitted through the third set of wires.

In certain embodiments, the cable allows a user to control one module from the other module irrespective of the software used by the other module.

In certain embodiments, the cable includes locking connectors at each end of the cable.

In certain embodiments, the software in the input module reprograms the software in the control module automatically upon connection of the input module to the control module and vice versa.

Other objects of the invention are achieved by providing an endoscopic system comprising: a input module; a control module; and a cable, the cable connecting the input module to the control module, the cable comprising: a first set of wires, the first set of wires allowing for video data to be transmitted across the cable, a second set of wires, the second set of wires allowing for image control data to be transmitted across the cable; a third set of wires, the third set of wires allowing for power control data to be transmitted across the cable; and pin connectors, the pin connectors being located on each end of the cable, such that each of the pin connectors corresponds to an individual electrical wire.

In certain embodiments, upon connection of the input module to the control module via the cable, software executes in the control module to transmit image control data through the second set of wires to determine if the software in the control module is compatible with the software in the input module.

In certain embodiments, the cable allows for image control data to be transferred between the input module and the control module through the second set of wires to program software files in either the input module or the control module, so that the input module is compatible with the control module.

In certain embodiments, after the software files in either the input module or the control module are programmed, power is automatically cycled to the module whose software files have been programmed.

In certain embodiments, the cable allows for control of the input module from the control module and vice-versa through the second set of wires.

In certain embodiments, the cable allows for the input module to be electrically linked to the control module at power-up.

In certain embodiments, the cable allows for the input module to be electronically linked to the control module when plugging the cable between the input module and the control module, and wherein the input module and the control module are already powered up.

In certain embodiments, the cable allows for controlling the power state of the input module from the control module and vice-versa through the third set of wires.

In certain embodiments, the cable allows a user to control one module from the other module irrespective of the software used by the other module.

In certain embodiments, the software in the input module reprograms the software in the control module automatically upon connection of the input module to the control module and vice versa.

In certain embodiments, the input module has a first interface card and the control module has a second interface card, wherein the video data transmitted across the cable is processed by the first and second interface cards.

In certain embodiments, the input module receives video data from a camera head.

In certain embodiments, the input module converts the video data received by the camera head into a data format recognizable by the control module, and wherein the input module transmits the reformatted video data to the control module.

Other objects of the invention are achieved by providing an endoscopic system comprising: a first input module; a second input module; a control module; a first cable connecting the first input module to the control module, the first cable including a first set of wires, the first set of wires allowing for video data to be transmitted across the cable, a second set of wires, the second set of wires allowing for image control data to be transmitted across the cable, a third set of wires, the third set of wires allowing for power control data to be transmitted across the cable, and pin connectors, the pin connectors being located on each end of the cable, such that each of the pin connectors corresponds to an individual electrical wire; and a second cable connecting the second input module to the control module, the second cable including a first set of wires, the first set of wires allowing for video data to be transmitted across the cable, a second set of wires, the second set of wires allowing for image control data to be transmitted across the cable, a third set of wires, the third set of wires allowing for power control data to be transmitted across the cable, and pin connectors, the pin connectors being located on each end of the cable, such that each of the pin connectors corresponds to an individual electrical wire.

In certain embodiments, upon connection of the first input module to the control module via the first cable, software executes in the control module to transmit image control data through the second set of wires of the first cable to determine if the software in the control module is compatible with the software in the first input module.

In certain embodiments, upon connection of the second input module to the control module via the second cable, software executes in the control module to transmit image control data through the second set of wires of the second cable to determine if the software in the control module is compatible with the software in the second input module.

In certain embodiments, the system further comprises an auxiliary input module.

In certain embodiments, the system further comprises a third cable, the third cable connecting the auxiliary input module to the control module, the third cable including a first set of wires, the first set of wires allowing for video data to be transmitted across the cable, a second set of wires, the second set of wires allowing for control data to be transmitted across the cable, a third set of wires, the third set of wires allowing for power control data to be transmitted across the cable, and pin connectors, the pin connectors being located on each end of the cable, such that each of the pin connectors corresponds to an individual electrical wire.

In certain embodiments, upon connection of the auxiliary input module to the control module via the third cable, software executes in the control module to transmit image control data through the second set of wires of the third cable to determine if the software in the control module is compatible with the software in the auxiliary input module.

In certain embodiments, the control module is linked to a PC or external network via an Ethernet link.

In certain embodiments, the system further comprises a room camera and a PC, the room camera and the PC being linked to the auxiliary input module.

In certain embodiments, the first input module receives video data from a first camera head and second input modules receive video data from a second camera head.

In certain embodiments, the first camera head and the second camera head transmit video data in different formats.

In certain embodiments, the first input module converts the video data received by the first camera head into a data format recognizable by the control module, and wherein the second input module converts the video data received by the second camera head into a data format recognizable by the control module.

Other objects of the invention are achieved by providing a method for reprogramming modules in a modular system in a medical operating room, the method comprising the steps of: providing a input module and a control module; and connecting the input module via a cable to the control module, such that upon connection of the input module to the control module via the cable, software in the control module determines the compatibility of software in the input module, and such that upon connection of the control module to the input module, the cable allows for electrical data to be transferred from the control module to the input module and vice-versa, to reprogram software files in either the control module or the input module, so that the input module is compatible with the control module.

In certain embodiments, after the software files in either the control module or the input module are reprogrammed, the at least one electrical connection automatically cycles power to the module whose software files have been reprogrammed.

Other objects of the invention and its particular features and advantages will become more apparent from consideration of the following drawings and accompanying detailed description. It should be understood that the detailed description and specific examples, while indicating the preferred embodiment of the invention, are intended for purposes of illustration only and are not intended to limit the scope of the invention.

DETAILED DESCRIPTION OF THE INVENTION

Figure 1:
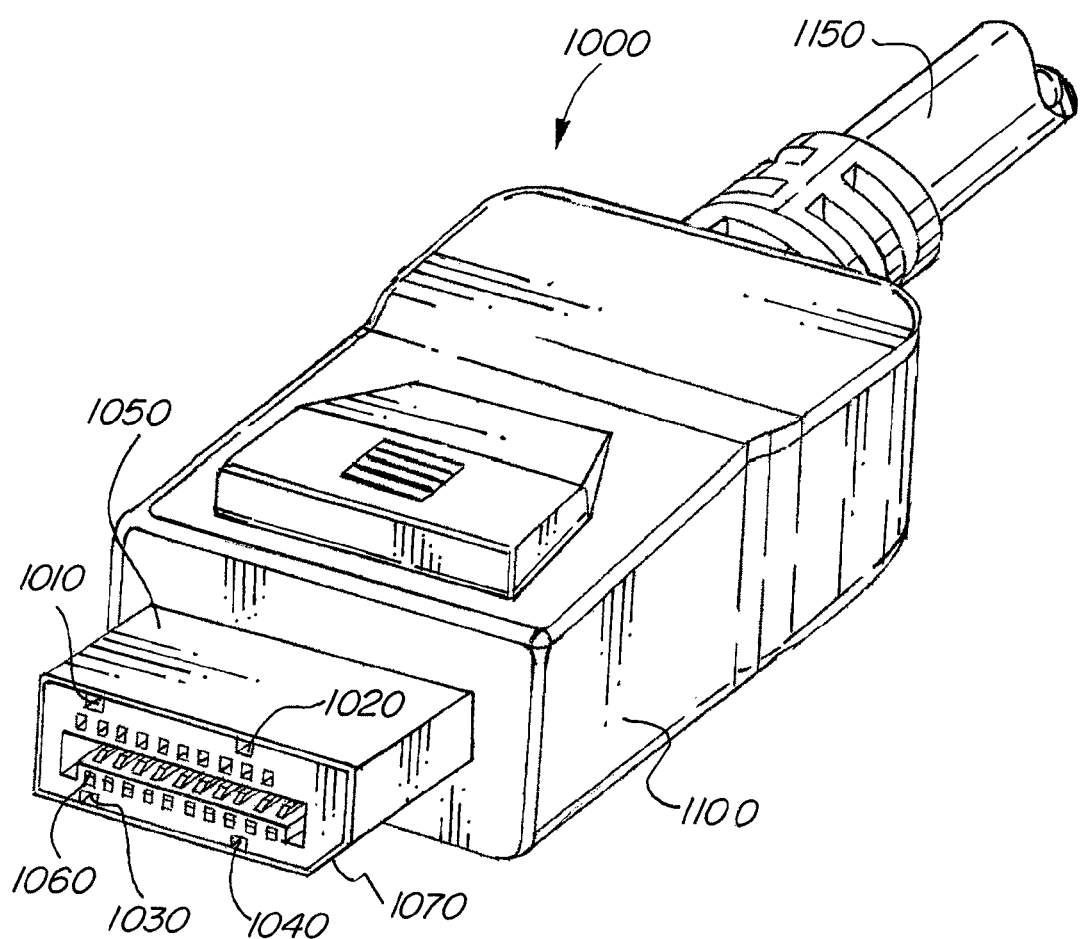
FIG. 1 is a perspective view of a cable of an embodiment of the invention.

Accordingly, the invention involves using a cable that functions as an inter-module link to link modules (such as an input module and a control module), which are developed, sold and installed at different times. A video system may be initially installed with a couple of modules, for example, and later an additional module can be added to a system in situ.

A cable is provided that allows for intercompability between the modules, such that the modules are forwards and backwards compatible with one another. This allows later developed modules incorporating various technologies and incorporating evolving industry standard interfaces as they evolve into an endoscopic system without having to re-design the entire system. This concept is known as modularity and allows the system to be modular in the fact that one unit can be replaced for another without replacing the entire system. Furthermore, the cable provides the ability to link new modules and accommodate future video camera system improvements and adaptations as current technology limitations are overcome, without obsolescing initial customer investments in control modules and allows one to take advantage of new features and functions of one module without requiring redesign and/or replacement of the entire system.

For example, the industry standard display and recording infrastructure technologies evolve at a different rate than, say, the video endoscope technology or the proximal camera head technology. So, by having a modular input module connected to a control module via a cable where the modular input module is forward and backward compatible with the control module, new camera technologies may be provided to replace outdated camera technologies, while still be compatible with older control modules as a result of the cable, and software executing within the control module through the cable.

Thus, a user can replace existing control modules with newer control modules that allow for a display having higher resolution or more color bit depth or 3D. Similarly, a user can replace an existing camera heads connected to input modules without replacing the control module or the display.

This provides a competitive advantage by being able to provide newer systems faster and users benefit from the backwards and forwards compatibility of the modules, as users only need to purchase the singular modules and not the entire system at any given time.

The cable or data link may be used in a modular imaging system that allows for increased flexibility for the consumer. The modular imaging system allows upgradeability and compatibility with a multitude of camera heads that are supported by a plurality of input modules, where the camera heads and input modules may be existing or yet to be developed. In old system, when a new imaging technology became available, a CCU could be incompatible with the new technology due to a variety of constraints, for example, hardware.

By using a modular architecture, the new technology can be supported by an input module that is compatible with the control module. In order to streamline the flexibility of the modular architecture, it is important to have an efficient way to re-program or re-configure the modular input module and control modules, including software, firmware, drivers etc.

In the modular system, software is loaded onto the control module and there is no need for the user to follow a particular set of steps to configure both old and new modules to work together. Instead, the user loads a bundle of software onto the control module, and the software is installed for each module that needs updating without the need to separately, boot, install, configure, program, re-boot, etc., each module. The bundle of software contains all files necessary for updating the modular system, and a cable between the control module and each input module allows for the control module to install software onto each input module as necessary as software is transmitted from the control module to the input modules in some embodiments.

In some embodiments, a compatibility check can be done for software and hardware with limited interaction from the user. The modular architecture increases the likelihood that existing visualization technology and yet to be developed visualization will be able to operate with some if not all of the same image processing hardware. This results in decreased capital costs for physicians offices, surgical offices and/or hospitals.

In certain embodiments, the control module may be designed to accommodate general image processing and display functions for multiple camera types or families. These general functions include, for example, user interface, image capture and streaming functionality as well as input/output functionality for the display/monitor interfaces, system interface and control, and network connectivity. The control module may be designed to accommodate one or multiple input modules. The control module may be connected to a display or the control module includes a display as a one piece unit. The control module may include a processor as well.

In the example of a control module that supports only one input module at a time, the overall modular system can be purchased at a lower initial cost. If the consumer wishes to purchase different camera or input module types, the modular system may be re-programmed to work with different imaging technology. If the control module supports multiple input modules, the consumer may still purchase new imaging technology, cameras and/or input modules, and still use the same control module once the re-programming is completed.

The input modules support all functions required for a group or family of image sources, such as cameras or auxiliary inputs. The input module provides compatibility between the family of image sources and the control module. Over the life of the system, additional input modules may be purchased to support emerging imaging technology such as 3D imaging, advanced fluorescence imaging, solid-state variable direction of view endoscopes, wireless camera heads and the like.

The group of input modules connected to the control module may further include an auxiliary input module. This module supports a variety of video sources such as third party camera control units, C-Arm, X-Ray, Ultrasound, Personal Computers and the like. Supported input formats may include DVI, VGA, S-Video, Composite, 3G-SDI and the like. Inputs may be both automatically and manually selected. The auxiliary module provides increased backward compatibility, forward compatibility and third party image source compatibility.

The re-programmability function of the modular architecture allows for economical buyers to progressively upgrade their imaging technology, rather than being required to purchase a camera control unit that is compatible with the entire range of imagers that the buyer would wish to purchase in the future. The efficient re-programmability function allows for hardware upgrades through input modules as well as software feature upgrades. The re-programmability function further minimizes the likelihood that newly purchased visualization technology will become obsolete while increasing backward compatibility of upgrades. Further, the cost of ownership and upgrade, such as acquisition, back-up, and maintenance, is reduced.

The streamlined re-configurability of the modular system further allows software features to be selectively activated in a cost effective manner. The modular control module may be connected to a data connection such as Internet or Ethernet, which allows the software updates to be purchased or verified online, with the files sent to the control module through the data connection.

Referring now to the drawings, wherein like reference numerals designate corresponding structure throughout the views.

FIG. 1 is a perspective view of an end of a cable 1000 according to an embodiment of the invention. As shown in FIG. 1, cable 1000 includes a connector 1100 connected to a cable connection 1150. The connector 1100 includes a pin holder 1050 located at the distal end of the cable 1000. The pin holder 1050 includes pin connectors 1060 and locking connectors 1010, 1020, 1030 and 1040 that attach the distal end of the cable to the input module or the control module. The pin holder 1050 as shown has a trapezoidal shape 1070. In other embodiments, the pin holder 1050 may have other shapes.

In certain embodiments, the pin connections 1060 may form a male/female connection with a slot in the input module or control module. In certain embodiments, the pin connectors 1060 are male and in other embodiments, the pin connectors are female.

In certain embodiments, the pin connectors 1060 have each pin connector corresponding to an individual wire in the cable connection 1150. The cable 1000 has another end having the same configuration as connector 1100. In some embodiments, one end of the cable is a male end and the other end of the cable is a female end. In other embodiments, both ends of the cable are male ends. In other embodiments, both ends of the cable are female ends.

Figure 2:
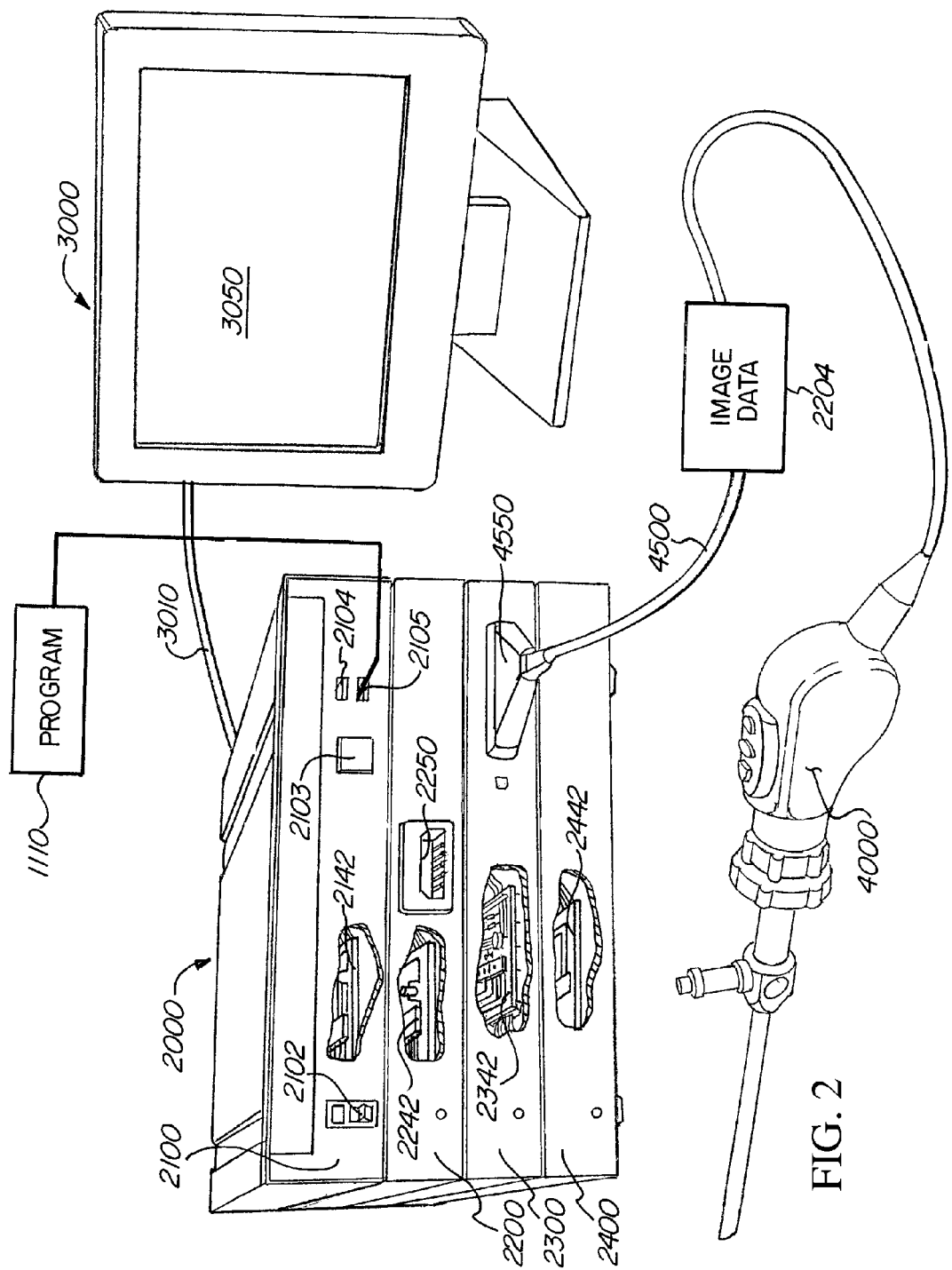
FIG. 2 is a perspective view of the endoscopic system including input modules and the control module connected by the cable of FIG. 1.

FIG. 2 shows a perspective view of the endoscopic system including input modules 2200, 2300 and 2400, and the control module 2100 stacked upon one another. Control module 2100 is shown connected to display 3000. In certain embodiments, the control module 2100 may be separate from the display 3000 and in other modules the control module 2100 may form a one-piece unit with the display. In certain embodiments, the display has a screen 3050, which may be a touch screen.

Internal portions of input modules 2200, 2300 and 2400 are also shown in FIG. 2. Input module 2300 is shown having an interface card or processor 2342 that converts video data received from the camera head 4000 into a format that is compatible with the control module 2100. Similarly, input module 2200 is shown having an interface card/processor 2242 and input module 2400 is shown having an interface card/processor 2442. Interface card/processor 2242 and 2442 convert video data received from the camera head 4000 into a format that is compatible with the control module 2100. In certain embodiments, each input module is able to process data in different formats, which is accomplished by differing interface card/processor(s).

The camera head 4000 is shown connected to input module 2300 by a cable 4500. Cable 4500 has a connector 4550 that connects into a slot such as shown in input module 2200 as slot 2250. Camera head 4000 may send image data 2204 to the input module through the cable 4500. Cable 4500 is different than cable 1000.

Control module 2100 is shown having an on/off switch 2102, which, in certain embodiments, can control the power of all of the input modules 2200, 2300 and 2400.

Control module 2100 is also shown having input slots or ports 2104 and 2105 as well as a white balance control switch 2103. In certain embodiments, the control module may receive a program 1110. In the present example, the program 1110 is received through a port 2105, however the program 1110 may be received through other port or data connection types as would be apparent to one of skill in the art. The program reprograms one or multiple processors 2142, 2242, 2342.

Figure 3:
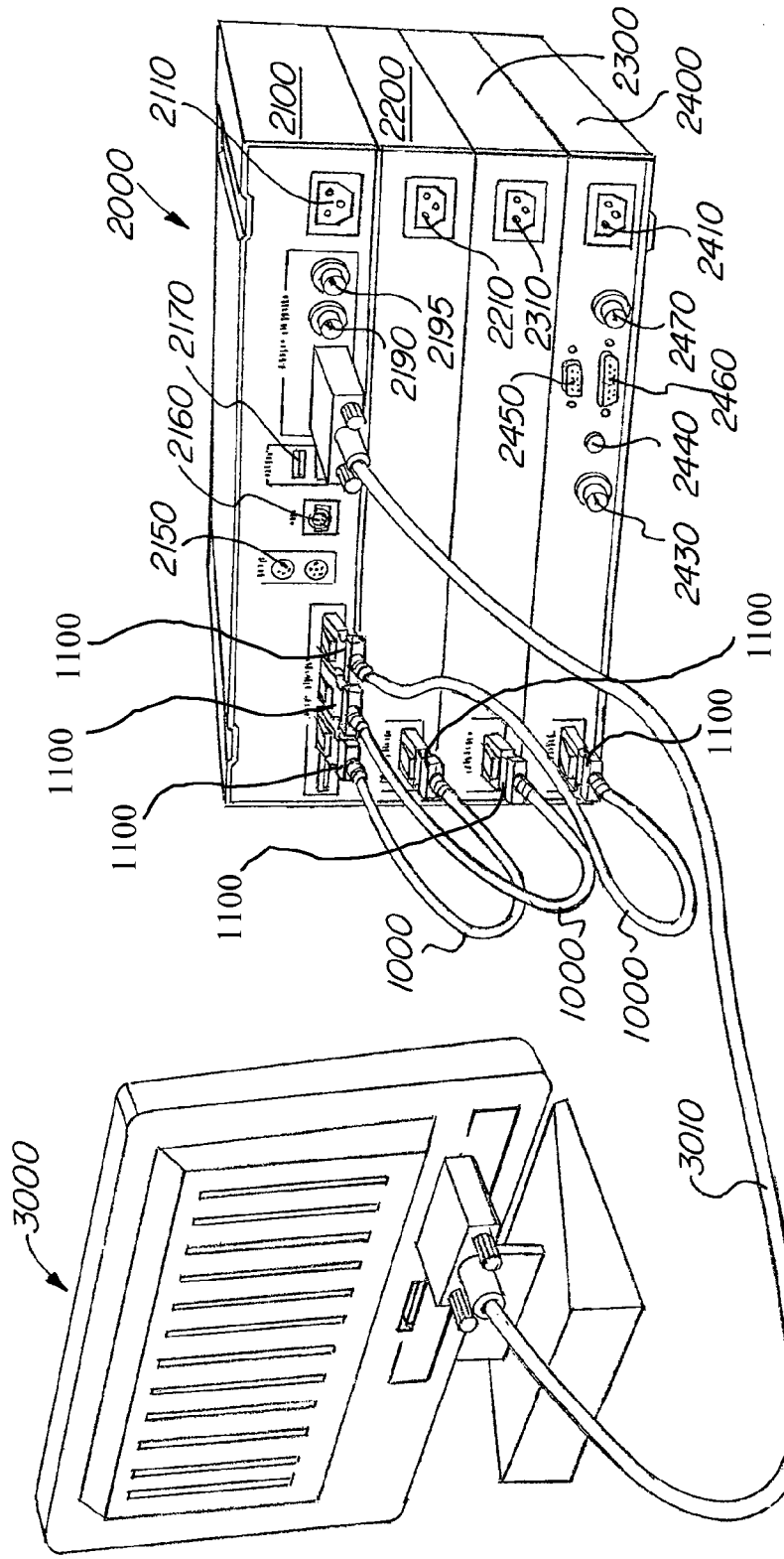
FIG. 3 is a perspective view of the endoscopic system including input modules and the control module connected by the cable of FIG. 1.

FIG. 3 shows control module 2100 being connected to input modules 2200, 2300 and 2400 via cables 1000, having connectors 1100 attached to one another. FIG. 3 also shows display 3000 connected to control module 2100 via cable 3010.

FIG. 3 shows input modules 2200, 2300 and 2400 each having a power plug 2210, 2310 and 2410 respectively. Control module 2100 is shown having four slots for receiving cables 1000, but may be designed having additional slots for receiving cables. Control module 2100 also has various output and input elements 2150, 2160, 2170, 2180, 2190 and 2195 to connect to various other input and output devices. Such devices may include a printer, external storage, and/or other such devices. Other example input/output elements may include DVI output for a DVI monitor or recorder, and a 3G SDI output for 3G SDI monitors or recorders.

Input modules 2200, 2300 and 2400 each have one slot respectively for receiving the cable 1000, but may have additional slots for receiving additional cables in other embodiments. Input module 2400 has various output and input elements 2430, 2440, 2450, 2460 and 2470 to connect to various other input and output devices. Other additional input and output elements may be envisioned for the various input modules 2200, 2300 and 2400.

Figure 4:
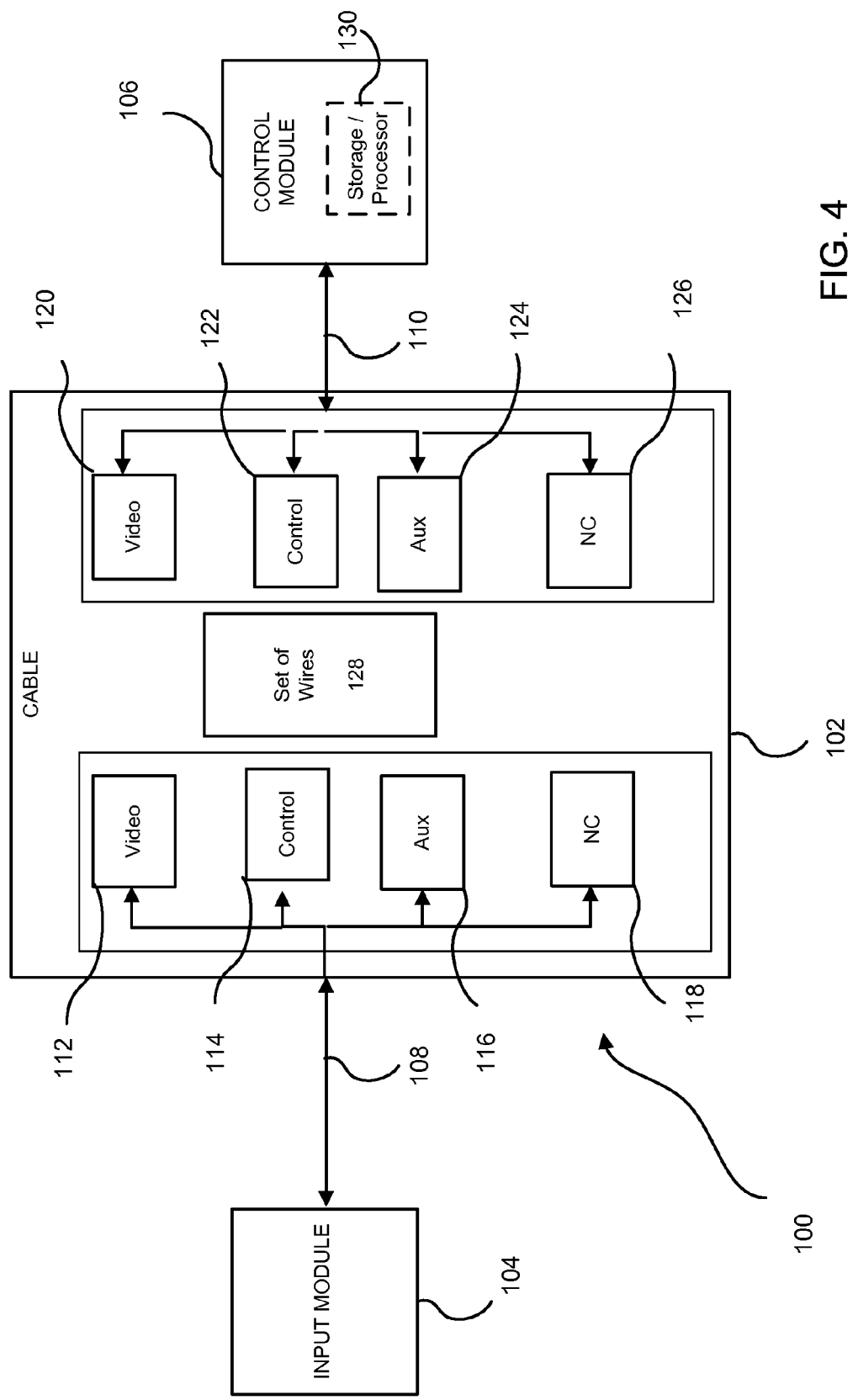
FIG. 4 is a schematic diagram of the endoscopic system of FIG. 3.
Figure 10:
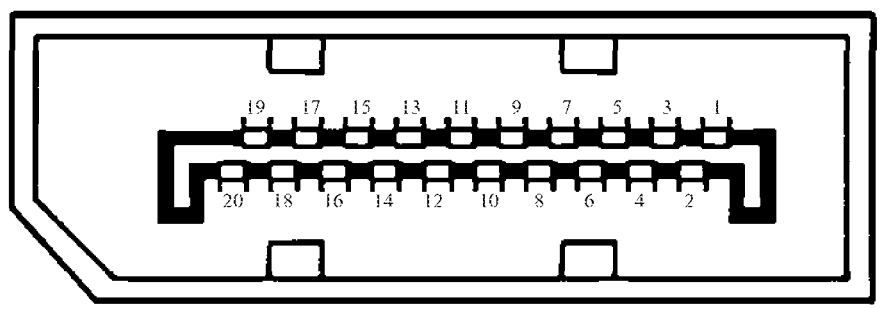
FIG. 10 is side view of the pin connections of the cable of FIG. 1.

FIG. 4 shows endoscopic system 100 including an input module 104. Input module 104 is connected to cable 102 via a first coupling connection 108. Coupling connection 108 may be hot-pluggable and may be a locking connector. Coupling connection 108 may use various pins to connect the cable 102 to the input module 104 as shown in FIGS. 1 and 10 and as described in Table 1 below.

TABLE 1

| Input Module (IM) # PIN Number | Signal Name | Control Module # Pin Number | Sublink |
|---|---|---|---|
| Pin 12 | IM_TMDS_Clock− | Pin 1 | Video |
| Pin 11 | IM_TMDS_Clock_Shield | Pin 2 | Video |
| Pin 10 | IM_TMDS_Clock+ | Pin 3 | Video |
| Pin 9 | IM_TMDS_Data0− | Pin 4 | Video |
| Pin 8 | IM_TMDS_Data0_Shield | Pin 5 | Video |
| Pin 7 | IM_TMDS_Data0+ | Pin 6 | Video |
| Pin 6 | IM_TMDS_Data1− | Pin 7 | Video |
| Pin 5 | IM_TMDS_Data1_Shield | Pin 8 | Video |
| Pin 4 | IM_TMDS_Data1+ | Pin 9 | Video |
| Pin 3 | IM_TMDS_Data2− | Pin 10 | Video |
| Pin 2 | IM_TMDS_Data2_Shield | Pin 11 | Video |
| Pin 1 | IM_TMDS_Data2+ | Pin 12 | Video |
| Pin 13 | IM_UART_TX | Pin 13 | Control |
| Pin 14 | IM_UART_RX | Pin 14 | Control |
| Pin 15 | IM_Aux+ | Pin 15 | Aux |
| Pin 16 | IM_Aux_Shield | Pin 16 | Aux |
| Pin 17 | IM_Aux− | Pin 17 | Aux |
| Pin 18 | IM_PWR_ENABLE | Pin 18 | Control |
| Pin 19 | IM_Return | Pin 19 | Control |
| Pin 20 | NC (No Connect) | Pin 20 | NC |

In FIG. 4, cable 102 is provided with at least two pins, including, at least one Video Pin 112, at least one Control Pin 114, at least one Auxiliary Pin 116 and at least one NC (no connect) pin 118. The video pin may be a Standard-Definition (SD) Pin or a High-Definition (HD) Pin. As used in this application, SD generally refers to a line count of up to approximately 720×480 NTSC and PAL; while HD refers to systems that utilize a higher line count and may include, for example but not limited to, 1280×720 progressive or 1920× 1080 or interlaced, which are only two of the commonly used HD resolutions. Depending on the camera type (SD or HD) the input module 104 will either transmit signals via an HD pin or an SD pin.

Also shown in FIG. 4 is a set of wires 128 shown in cable 102. The cable 102 uses the set of wires 128 to connect the input module 104 to the control module 106. The set of wires 128 each correspond to an individual pin connector as shown in FIG. 1. The set of wires 128 include a first set of wires, the first set of wires allowing for video data to be transmitted across the cable; a second set of wires, the second set of wires allowing for image control data to be transmitted across the cable; and a third set of wires, the third set of wires allowing for power control data to be transmitted across the cable.

The second set of wires allows the input module 104 and control module 106 to be forward and backwards compatible with each other as data is transferred over the second set of wires in the cable 102. In certain embodiments, the second set of wires allows for updating the software of the input module and/or the control module through electrical signals transmitted between the modules and through the cable.

The cable 102 also includes at least one Video Link 120, at least one Control Link 122, at least one Auxiliary Link 124 and at least one NC Link (no connect) 126. These links interact with the control module 106 to transmit electrical signals to the control module 106 across the set of wires 128. It is contemplated that control module 106 may have a display attached to the control module. It is contemplated that the input module 104 may be attached to an endoscope or camera head via a cable.

In certain embodiments, upon connection, software in the input module 104 can be used detect the control module 106 when the cable 102 attaches the input module 104 to the control module 106. In certain embodiments, the software can determine the correct signal format for proper functioning of control module 106. For example, control module 106 may be designed to display only SD video signals. That being the case, cable 102 will transmit an SD signal format to control module 106 whether an SD or an HD camera is connected. Alternatively, it may be determined that the control module 106 may be designed to display HD video signals. In this case, if the input module 104 is connected to an HD camera, an HD signal is transmitted to the input module, which is then transmitted to the control module 106 across cable 102. If however, if the input module 104 is connect to an SD camera, an enhanced SD signal may be transmitted across the cable 102 to the control module 106, which is connected to an HD display. In this manner the following signal format types may be used $SD_{input} \rightarrow SD_{output}$; $SD_{input} \rightarrow$ Enhanced $SD_{output}$; $HD_{input} \rightarrow SD_{output}$; and $HD_{input} \rightarrow HD_{output}$. It should be noted that categorization of inputs and outputs as SD or HD is not intended to limit the categories to a single signal format, but rather, many differing signal formats may be categorized as SD and many differing signal formats may be categorized as HD.

It is contemplated that configuration information for either input module 104 and/or control module 106 may be located on software executing on the input module 104 and control module 106 respectively. In certain embodiments, input module 104 and control module 106 may each have an interface card (2350 for as shown in FIG. 2) that converts video data received by the camera head 4000 into a format that is compatible with the control module 2100.

In certain embodiments, the control module 106 has storage/processor 130. In certain embodiments, the control module is connected to, for example, an Intranet, the Internet and/or the like. In certain embodiments, the input module 104 and/or the control module 106 includes WIFI and/or a way to receive information directly from the Internet, either wired or wirelessly.

In certain embodiments, the cable 102 allows for electronic signals from software executing on the input module 104 and the control module 106 to allow for the input module 104 and control module 106 to be forwards and backwards compatible with one another.

Figure 7:
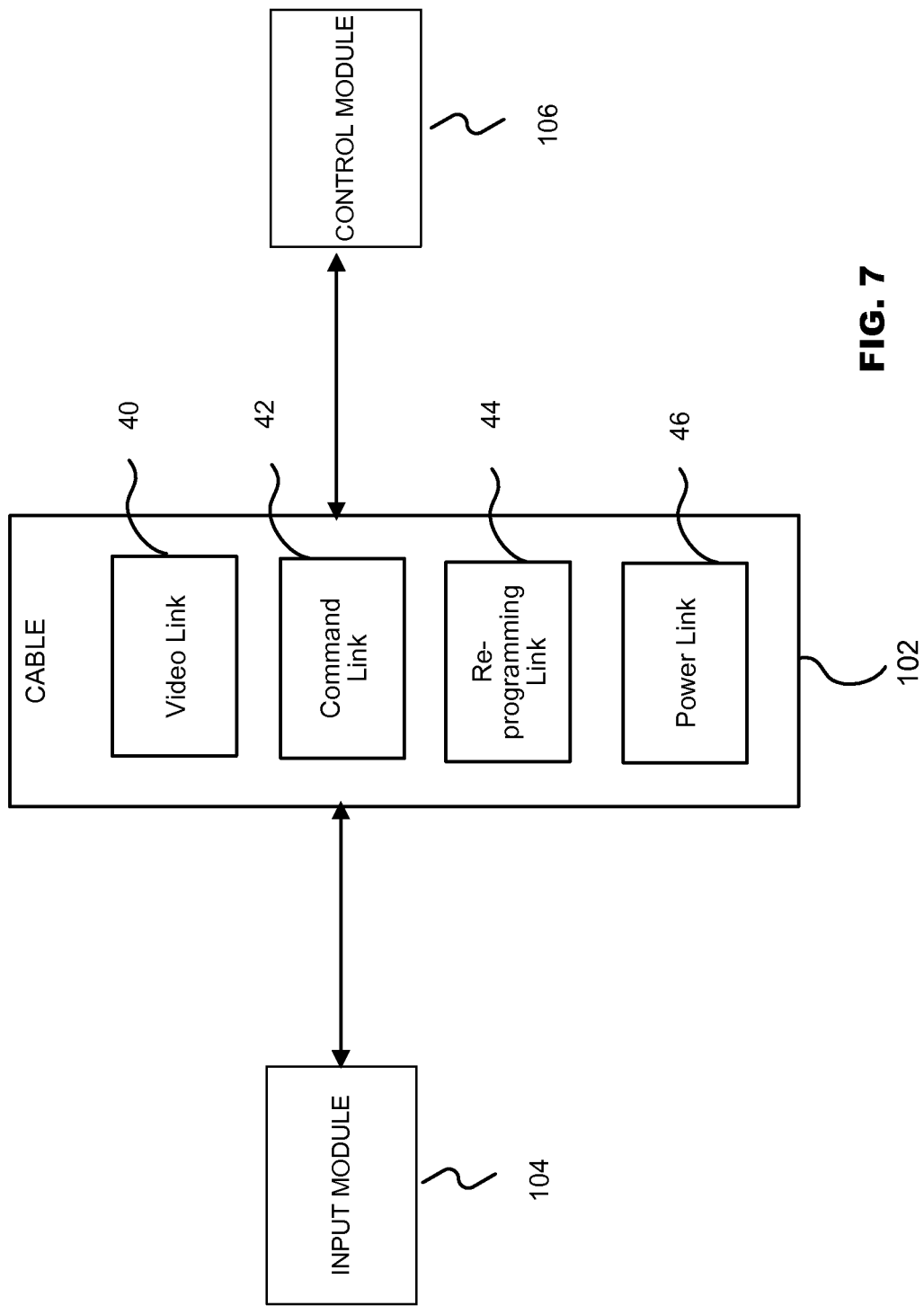
FIG. 7 is a schematic diagram of the endoscopic system of FIG. 3.

In certain embodiments, the cable includes a video link 40, a command link 42, a reprogramming link 44 and a power link 46 as shown in FIG. 7. In certain embodiments, these links are associated with pin connections as shown in FIG. 10. In certain embodiments, the video link 40 is associated with certain pins, and the command link 42, reprogramming link 44 and power link 46 are all associated with separate pins in the cable. In certain embodiments, the video link 40 involves one or more wires, where the one or more wires correspond to individual pins as shown in Table 1.

In certain embodiments, each of the video links 40 is associated with certain pins, and the command link 42, reprogramming link 44 and power link 46 are associated with separate optical fibers within cable 102.

The video link 40 is capable of sending digital video in the form of HD and SD video over the cable from module to module at fully run-time programmable image sizes, color spaces, bit-depths and frame-rates. The receiving and transmitting ends of the video signals can auto-negotiate these various parameters using the various pins shown in FIG. 10.

The command link 42 is used by the module receiving the Video Link 40 (e.g. a Display Control Module) to interact with the module sending the Video Link (e.g. Head Interface Module or Auxiliary Input Module). In certain embodiments, the command link 42 may establish connections between modules at power-up and/or when hot-plugging the cable connection between modules that are already powered-up.

In other embodiments, the command link 42 may determine inter-module compatibility of both hardware and software/firmware for the purpose of backward and forward compatibility of operation. The command link 42 is associated with the optical wire 128 in the cable.

In other embodiments, the command link 42 may determine inter-module compatibility of both hardware and software/firmware for the purpose of re-programming one module with the other to bring one module up to the compatibility of the other module.

In other embodiments, the command link 42 may publish the functionality of one module to the other module in order to run-time configure and control the feature set of one module from the other irrespective of the release dates of each module (e.g. an input module can be released much later than the control module and the control module would still be able to display the user interface and control the new commands that the input module publishes.

In other embodiments, the command link 42 may control the features and report status of one module from the other module.

In certain embodiments, the reprogramming link 44 is used by one module to re-program other modules' re-programmable files.

In certain embodiments, the power link 46 is used by one module (e.g. the control module) to control the power state of the other modules (e.g. input module or auxiliary input module).

In certain embodiments, the power link 46 programmatically controls the power state of one module from the other (e.g. automatically cycle power on the Head Interface module after re-programming it).

Figure 5:
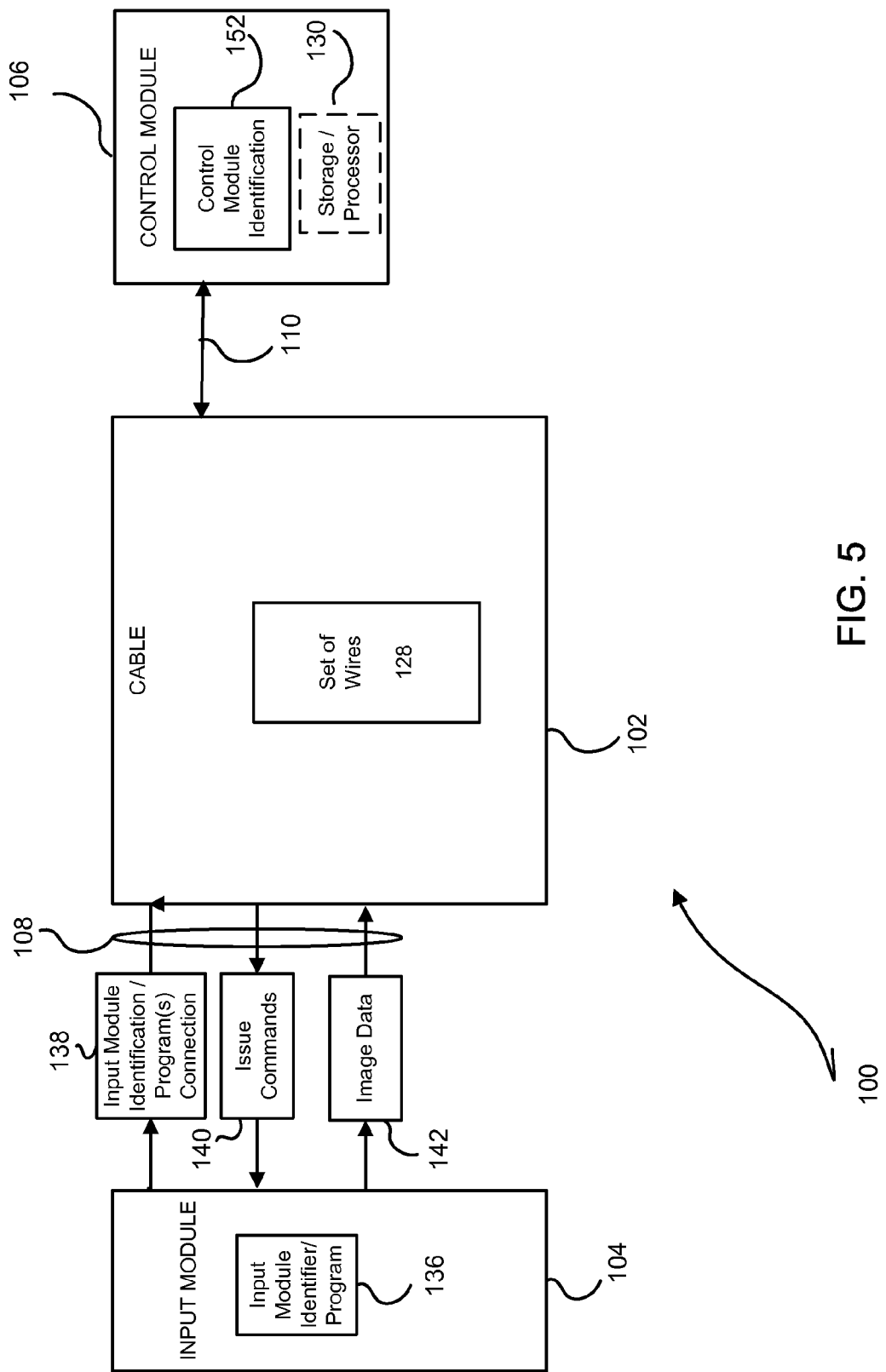
FIG. 5 is a schematic diagram of the endoscopic system of FIG. 3.

Referring now to FIG. 5, an advantageous embodiment of the interaction between input module 104 and cable 102 is illustrated. For example, upon connection of input module 104 to cable 102, input module identifier/program 136 stored on input module 104 may be transmitted as input module information/program(s) 138 to cable 102. It is contemplated that the input module identifier may comprise discrete data or may comprise a program. In addition, it is contemplated that one or more programs may be stored on input module 104 and transmitted as or with the input module identification data upon connection of the input module 104 to the control module 106 via the cable 102. As shown the data or program is transferred through connector or interface 108. As shown, the control module 106 receives the input module information/program(s) and may executes the program(s), which allows the software on the control module 106 to be reprogrammed according to the input module information/program(s) 138 transferred via cable 102.

It is further contemplated that one or more programs may be located on a storage/processor 130. In certain embodiments, the storage/processor 130 is located remote from the input module 104 and control module 106.

In certain embodiments, upon connection of input module 104 to cable 102 to the control module 106 issue commands 140 may be transmitted to the input module 104. In certain embodiments, input module identifier/program 136 may be transmitted to cable 102 using the input module identification/program(s) connection 138. Once identified, a program(s) may be transmitted to control module 106.

In certain embodiments, software executing on the input module 104 may transmit image data 142 through cable 102 to control module 106. In certain embodiments, the control module 106 may have control module information 152 transmitted through cable 102 to input module 104. Commands issued to the input module 104 may include, for example, adjusting color balance, light, focal distance, resolution, zoom, focus, shading, and other optical characteristics if the input is a camera video or video endoscope. Input module 104 may then generate and transmit image data 142, which is transmitted by cable 102 to control module 106 in the proper signal format to control module 106.

Figure 6:
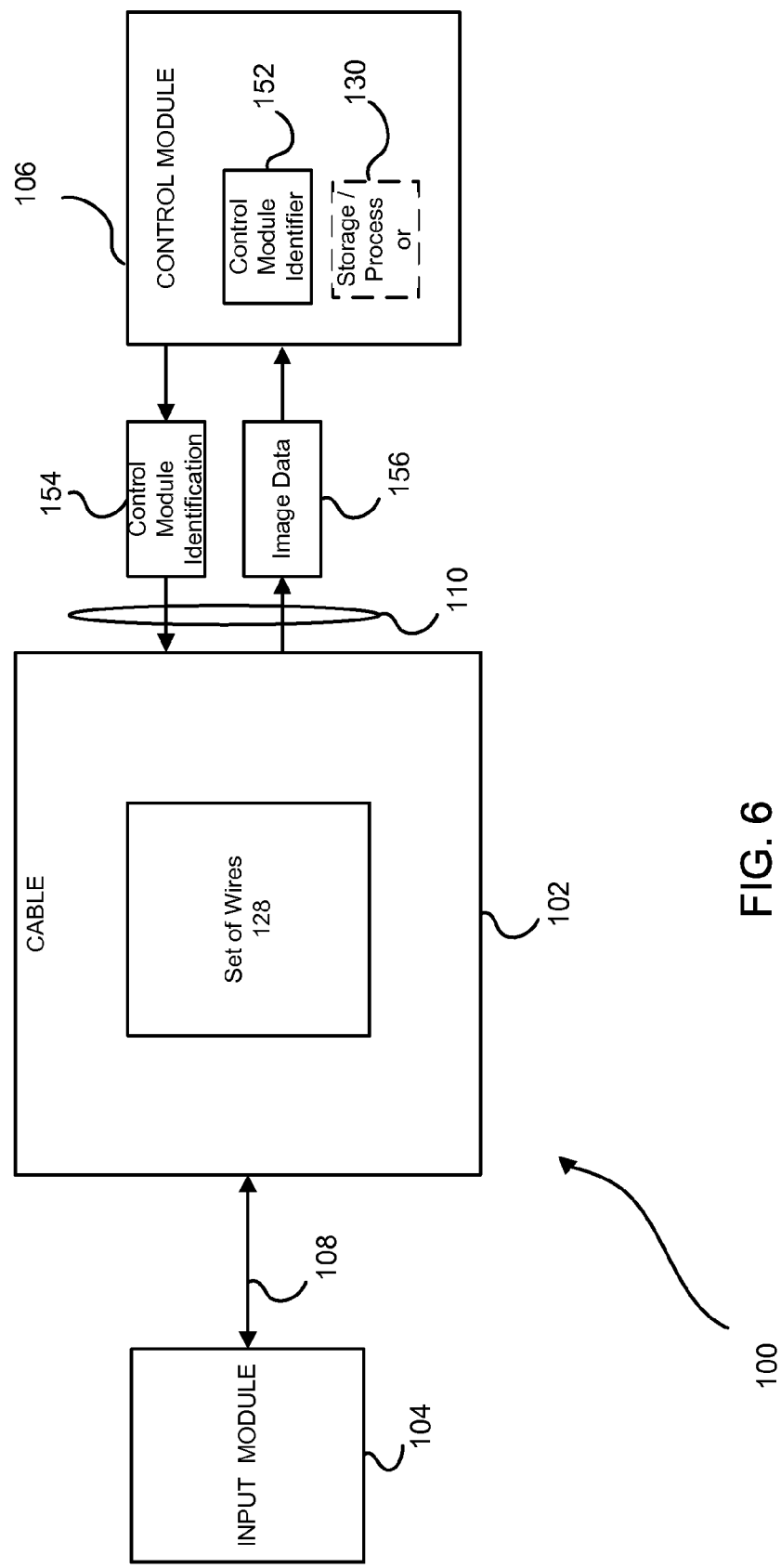
FIG. 6 is a schematic diagram of the endoscopic system of FIG. 3.

FIG. 6 illustrates still another advantageous embodiment of the system 100. In this embodiment, control module identifier 152 stored on control module 106 is transmitted as control module identification 154 to cable 102. Once received, input module 104 will determine a signal format that will be compatible with control module 106. Image data 156 will then be transmitted to control module 106 in the properly configured signal format.

There are commonly used types of signal formats, however, it is contemplated that additional formats may be provided for and especially new signal formats that may become available. The two commonly used SD format types are NTSC and PAL. It should be noted that these are just two video signal formats and that there are many differing types and modifications to the above-listed types including, for example, a modified version Phase-Alternating Line (PAL-M). In any event, upon receipt of control module information 154 transmitted to input module 104, configuration of the output signal for sending image data 142 in the proper format can be sent to control module 106.

In addition to the standard NTSC and PAL SD (NTSC and PAL) composite, RGB, and s-video (Y/C) outputs, numerous other outputs may be used. The following examples are presented to further illustrate and explain the present invention and should not be taken as limiting in any regard.

Serial Digital Interface (SDI), standardized in ITU-R BT.656 and SMPTE 259M, is a digital video interface used for broadcast-grade video. A related standard, known as High Definition Serial Digital Interface (HD-SDI), is standardized in SMPTE 292M and provides a nominal data rate of 1.485 Gbit/s.

Digital Visual Interface (DVI) is a video interface standard designed to maximize the visual quality of digital display devices such as flat panel LCD computer displays and digital projectors and is partially compatible with the HDMI standard in digital mode (DVI-D). The DVI interface uses a digital protocol in which the desired illumination of pixels is transmitted as binary data. When the display is driven at its native resolution, it will read each number and apply that brightness to the appropriate pixel. In this way, each pixel in the output buffer of the source device corresponds directly to one pixel in the display device.

High-Definition Multimedia Interface (HDMI) is an all-digital audio/visual interface capable of transmitting uncompressed streams. HDMI is compatible with High-bandwidth Digital Content Protection (HDCP) Digital Rights Management technology. HDMI provides an interface between any compatible digital audio/video source and a compatible digital audio and/or video monitor, such as a digital television (DTV).

In certain embodiments, input module identification program 138 is sent to the control module 106 and software executing on the control module 106 can compare program(s) versions from input module identification program 138 to determine if the input module identification/program(s) received from input module 104 is the latest version and if not, the input module and control module information can be updated. This can happen automatically, or the system could, for example, prompt the user to decide whether or not to update the first or control module information. In addition, it is contemplated that based upon user access, certain programs and/or features may become available.

In certain embodiments, the cable 102 allows for both forwards and backwards compatibility between the input module 104 and the control module 106. In certain embodiments, the set of wires 128 in the cable transmits electrical signals from input module 104 to control module 106 and vice versa that allows for various processes to occur.

Figure 8:
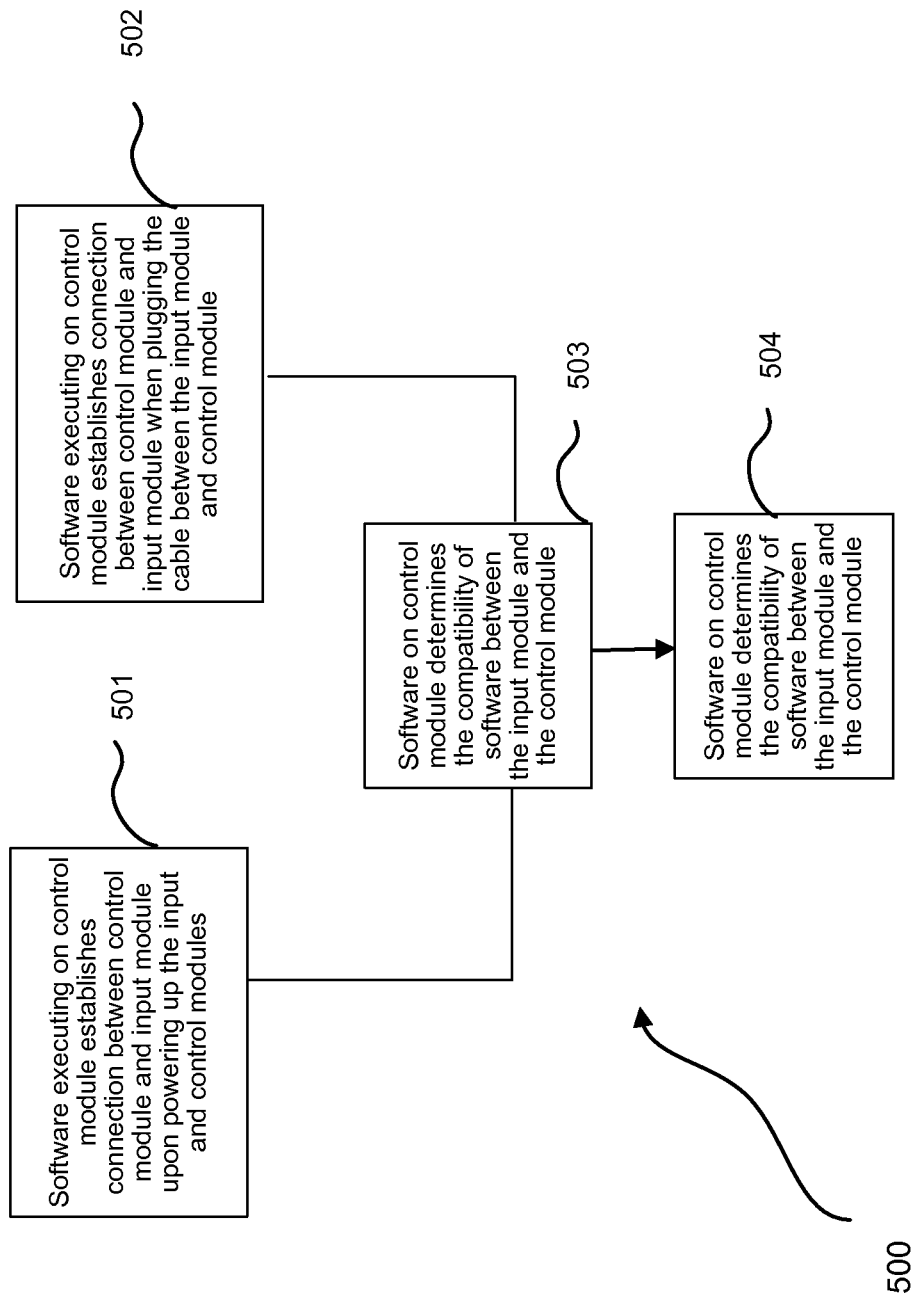
FIG. 8 is a flowchart of a process executed in the endoscopic system of FIG. 3.

Referring to FIG. 8, a flowchart of various processes of the cable 102 is shown. FIG. 8 shows that the software on control module establishes connection between control module and input module upon powering up the input module and control module 501 or the software on the control module establishes connection between control module and input module when plugging the cable between the input module and control module 502.

Afterwards, the software on the control module determines the compatibility of hardware between the input module and the control module 503 and then the software on the control module determines the compatibility of software between the input module and the control module 504.

Figure 9:
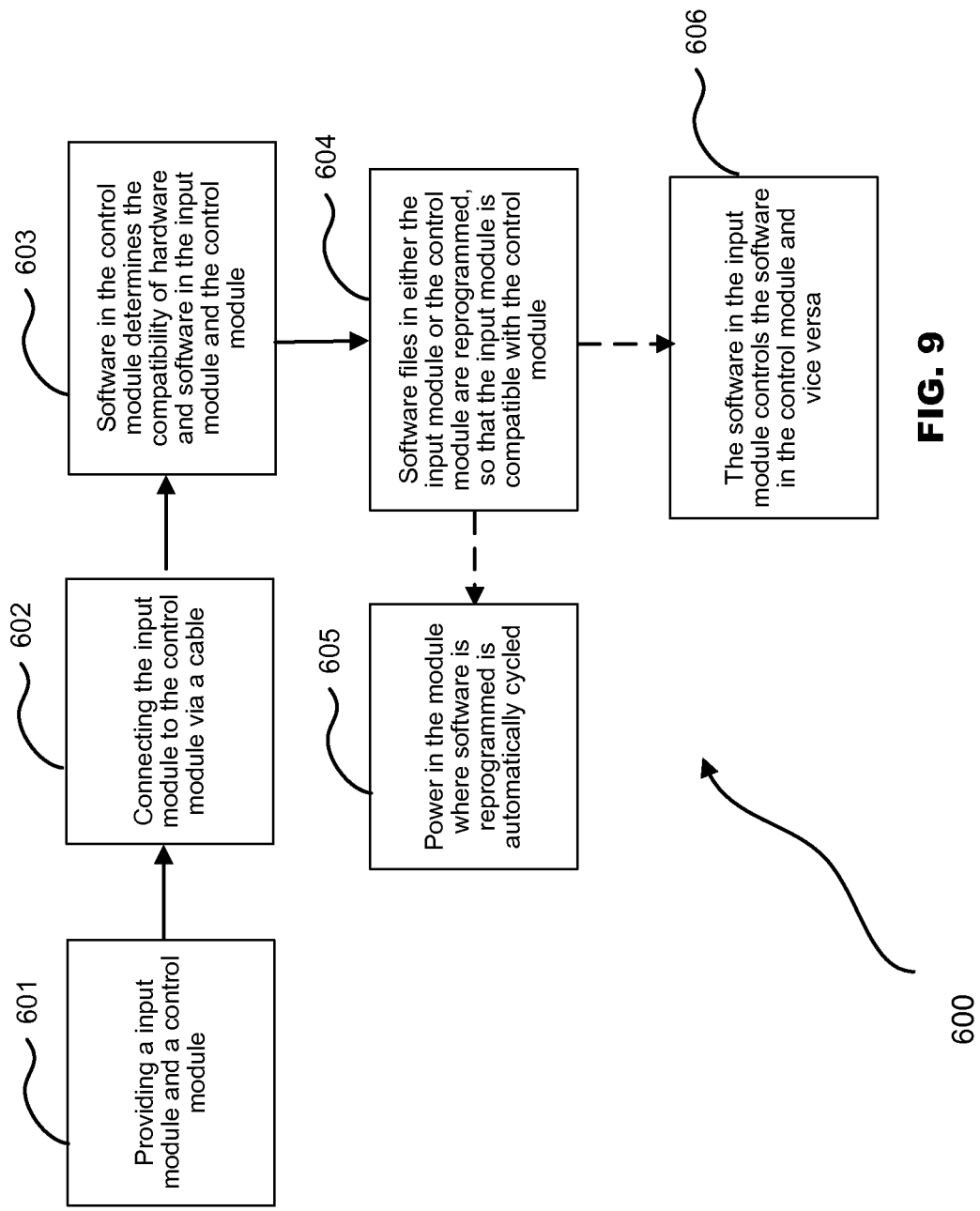
FIG. 9 is a flowchart of a process executed in the endoscopic system of FIG. 3.

FIG. 9 refers to a method for reprogramming modules in a modular system in a medical operating room 600, the method comprising the steps of: providing a input module and a control module 601, connecting the input module via a cable to the control module 602, software in the input module determines the compatibility of hardware and software in the input module and the control module 603 and software files in either the input module or the control module are reprogrammed, so that the input module is compatible with the control module 604.

In certain embodiments, the method includes the optional step of having power in the module where software is reprogrammed is automatically cycled 605.

In certain embodiments, the method includes the optional step of having the software in the input module controls the software in the control module and vice versa 606.

Other steps in the method may include the input module to be electronically linked to the control module at power-up. Also steps in the method may include the input module to be electronically linked to the control module when plugging the cable between the input module and the control module, and wherein the input module and the control module are already powered up. The software in the input module may reprogram the software in the control module automatically upon connection of the input module to the control module or vice versa.

Figure 11:
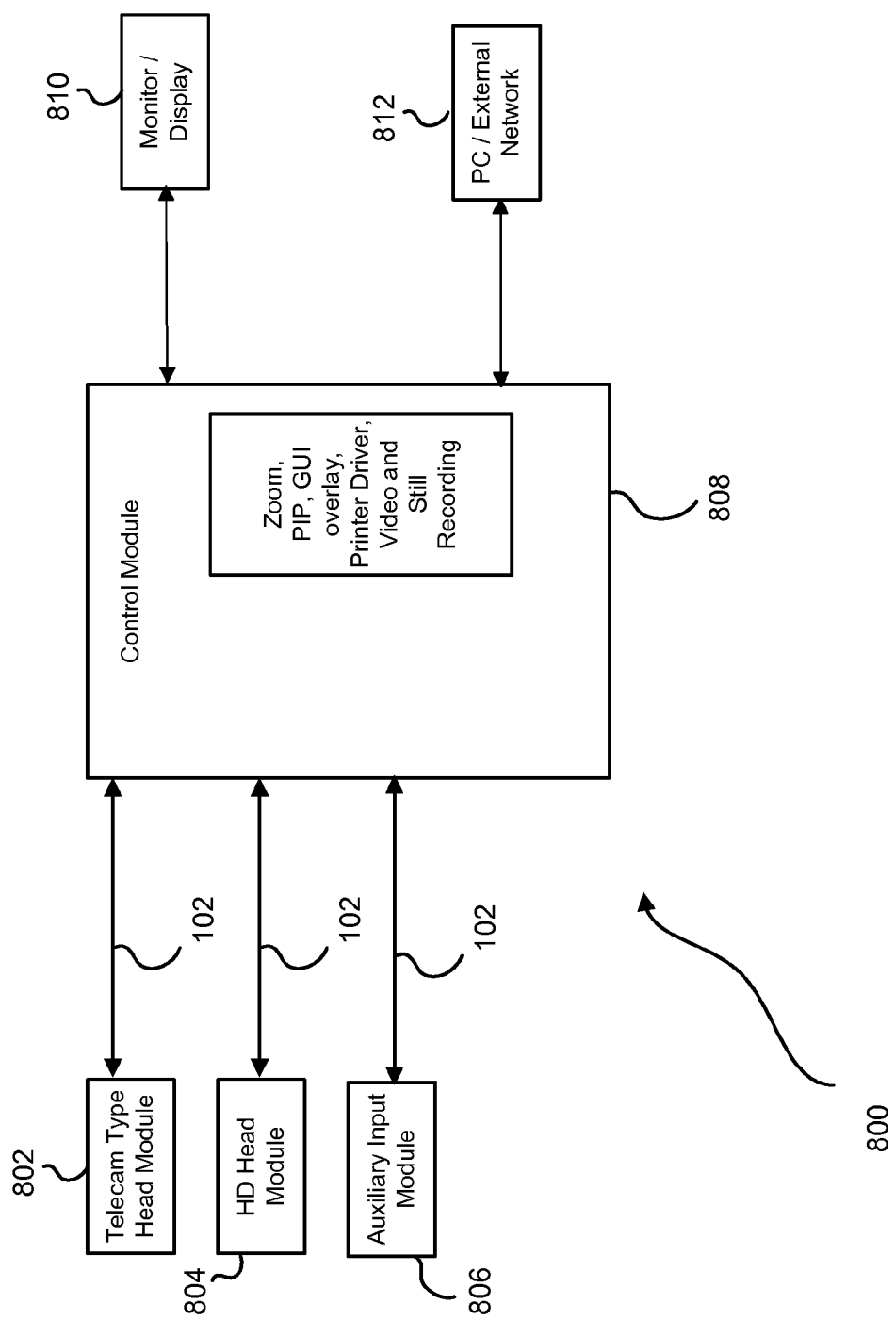
FIG. 11 is a flowchart of a process executed in the endoscopic system of FIG. 3.

Referring to FIG. 11, the cable 102 is shown being used to connect various modules to one another in a modular imaging system 800. Here, cable 102 is shown connecting SD type head module 802 to the control module 808. Separate cables are shown connecting the HD head module 804 and auxiliary input module 806 to the control module 808.

Also shown in FIG. 11 are a monitor 810 and PC/External Network 812. The monitor 810 and PC/External Network 812 are shown connected to the control module 808. The PC, External Network 812 can be connected to the control module 808 via an Ethernet link or network in certain embodiments.

In certain embodiments, the control module has various features associated with it including Zoom, PIP, GUI overlay, Printer Driver, Video and Still Recording.

In various embodiments, the single cable 102 connection is between two modules having the following sub-connections or sub-links: (1) A Video Link; (2) A Command and Status Link; (3) A Re-programming Link; and (4) A Power Enable/Disable Link.

In certain embodiments, the cable 102 includes a set of wires for transmitting electronic signals from the input module 104 to the control module 106. In certain embodiments, the cable is robust and flexible.

As shown above in Table 1, the Video Sublink Signals in Table 1 are compatible with the video portion of HDMI and with the input module and control module printed circuit boards with 0 to 2 meters of cable.

In certain embodiments, the Video Sublink Signals support 148.5 megapixels/sec at 24 bits/pixel (4:2:2, 12 bits Y and 12 bits Cb/Cr) plus overhead). The format of the signals over the link is a four-pair TMDS link with one pair for the clock and three pairs of 8 bits each per pixel for a total of 24 bits. The bit rate of the three pairs is 10 times the pixel rate. This means that the pairs shall be able to handle 1.485 Gbits/sec each.

In certain embodiments, optical fibers in the cable can handle clock speeds down to 24 MHz corresponding to 24 Mpixels/s. Formats that are slower than this shall add extra horizontal blanking to each line in order to increase the pixel rate above this lower limit.

In certain embodiments, the video source side of the cable (Head Modules and Auxiliary Input Modules) shall receive a control signal, PWR_EN over the Inter Module Link. When the cable is disconnected the Head Module/Auxiliary Input Module shall consider this signal as in the Power Enabled state (i.e. IM_PWR_ENABLE active). When the cable is connected the Display/Control Module side shall be able to de-activate the IM_PWR_ENABLE signal and thus disable the power supply in the Head Module/Auxiliary Input Module. The idea here being that the Head Module is normally powered-up when no cable is connected, so if a cable were inadvertently disconnected during operation the Head Module/Auxiliary Input module would stay powered up and ready to resume should the cable be plugged back in. This facilitates the rapid resuming of usable video image in such a case.

In certain embodiments, the cable is capable of being plugged in and un-plugged while either or both modules are powered-up.

In certain embodiments, if the cable is unplugged while IM_PWR_ENABLE is set to enabled (powered-up), the Head Modules/Auxiliary Input Modules shall not power-down as a result.

In certain embodiments, if the cable is unplugged while IM_PWR_ENABLE is set to disabled (powered-down) the Head Module/Auxiliary Input Module shall power-up.

In certain embodiments, the cable shall power down the bulk of its electronics when the IM_PWR_ENABLE signal is pulled low (disabled) buy the control module. Otherwise the input/auxiliary module(s) shall remain powered up whenever there is power on the AC mains.

In certain embodiments, the IML Aux Sublink Signals in the above Table are used as a half-duplex, high-speed arrangement. The direction of the interface is controlled from the Control Module using commands over the IML Comm Link.

In certain embodiments, the signaling protocol for the Control Sublink shall be a UART protocol: 8 bits, 1 start bit, 1 stop bit, no parity at 5 Mbits/sec.

In certain embodiments, upon power up, the default direction of the Aux Sublink shall be set such that the Control Module is in transmit mode and the Interface Module is set to be in receive mode.

In certain embodiments, the Aux Sublink channel is used for: 1) Reprogramming the FPGA Configuration files and other software files located in the FPGA Configuration Flash in the Head Modules/Aux Input Modules; and 2) Download to the Control Module the software files that contain the "published" information from the Head Modules/Aux Input Modules.

In certain embodiments, all signals include a method to determine connection and connection quality. Continuous monitoring suggested where practical (CRCs, 8/10b balance, etc. . . . ) or quality assessment on power up and reconfiguration (Bit Error test with Pseudo Random Bit Sequence, etc. . . . )

In certain embodiments, the Head Modules/Auxiliary Input Modules may use the Control Sublink Signals to determine that there is no connection to a Control Module (via a communications time out for example) and use this information to disable its Video Transmission.

Any device with an cable port shall be able to determine if it is connected to another device via a cable (assuming of course that both devices have power applied to the AC mains). Note: there is no special connection for this purpose, but the UART Rx line shall be normally pulled low at the receiving device so the receiving device can use the resulting continuous framing errors to determine that the other end is not connected. (Rx stuck at the "space" or "start bit" level for at least 10 bits will result in a framing error.) Of course, this scheme requires that the UART Tx line transmits a "mark" or "stop bit" level whenever there is nothing to send—which is the normal action for a UART.

In certain embodiments, the cable 102 includes color coding, connector key, locking and/or labeling to minimize the chance of wrong module connection.

While the invention has been specifically described in connection with certain specific embodiments thereof, it is to be understood that this is by way of illustration and not of limitation, and that various changes and modifications in form and details may be made thereto, and the scope of the appended claims should be construed as broadly as the prior art will permit.

The description of the invention is merely exemplary in nature, and, thus, variations that do not depart from the gist of the invention are intended to be within the scope of the invention. Such variations are not to be regarded as a departure from the spirit and scope of the invention.

What is claimed is:

1. A system for connecting an input module and a control module in a modular endoscopic imaging system, comprising:
   a control module;
   a plurality of input modules, each of the plurality of input modules adapted to be connectable with a camera, each of the plurality of input modules adapted to be connectable with the control module and to convert video data received from a connected camera into a data format recognizable by the control module;
   a cable having:
      a first set of wires, the first set of wires allowing for video data to be transmitted across the cable;

a second set of wires, the second set of wires allowing for image control data to be transmitted across the cable;

a third set of wires, the third set of wires allowing for power control data to be transmitted across the cable;

wherein upon connection of an input module to the control module via the cable, the input module one of the plurality of input modules, software automatically executes in the control module to transmit image control data through the second set of wires to determine if the software in the control module is compatible with the software in the input module, wherein the cable allows for image control data to be automatically transferred between the input module and the control module through the second set of wires to program software files in the input module, so that the input module is compatible with the control module, wherein the control module is adapted to control the power of the input module and, after the software files in the input module are programmed, power is automatically cycled to the input module, and wherein, upon connection of the input module to the control module, at least one of:
  software in the input module automatically reprograms software in the control module, and
  software in the control module automatically reprograms software in the input module.

2. The system of claim 1, further comprising a fourth set of wires, the fourth set of wires having an undefined function to allow for expansion of functionality across the cable.

3. The system of claim 1, wherein the cable transfers digital video data across the first set of wires.

4. The system of claim 3, wherein the digital video data is sent in run-time programmable images sizes, color spaces, bit-depths and frame-rates.

5. The system of claim 1, wherein the cable is double ended, such that either end of the cable is pluggable into the input module and the control module.

6. The system of claim 1, wherein the cable allows for control of the input module from the control module and vice-versa through the second set of wires.

7. The system of claim 1, wherein the cable allows for the input module to be electrically linked to the control module at power-up.

8. The system of claim 1, wherein the cable allows for the input module to be linked to the control module when plugging the cable between the input module and the control module, and wherein the input module and the control module are already powered up.

9. The system of claim 1, wherein the cable allows for controlling the power state of the input module from the control module and vice-versa through power control data transmitted through the third set of wires.

10. The system of claim 1, wherein the cable allows a user to control one of the input module and control module from another of the input module and control module irrespective of the software used by the another of the input module and control module.

11. The system of claim 1, wherein the cable includes locking connectors at each end of the cable.

12. The system of claim 1, wherein the software in the input module reprograms the software in the control module automatically upon connection of the input module to the control module and vice versa.

13. An endoscopic system comprising:
an input module adapted to be connectable with and receive video data from a camera head module;
a control module adapted to control the power of the input module;
the input module adapted to be connectable with the control module and to convert the video data into a data format recognizable by the control module; and
a cable, the cable connecting the input module to the control module, the cable comprising:
  a first set of wires, the first set of wires allowing for video data to be transmitted across the cable;
  a second set of wires, the second set of wires allowing for image control data to be transmitted across the cable;
  a third set of wires, the third set of wires allowing for power control data to be transmitted across the cable;
wherein upon connection of the input module to the control module via the cable, software automatically executes in the control module to transmit image control data through the second set of wires to determine if the software in the control module is compatible with the software in the input module,
wherein the cable allows for image control data to be automatically transferred between the input module and the control module through the second set of wires to program software files in the input module, so that the input module is compatible with the control module,
wherein after the software files in the input module are programmed, power is automatically cycled to the input module, and
wherein, upon connection of the input module to the control module, at least one of:
  software in the input module automatically reprograms software in the control module, and
  software in the control module automatically reprograms software in the input module.

14. The endoscopic system of claim 13, wherein the cable allows for control of the input module from the control module and vice-versa through the second set of wires.

15. The endoscopic system of claim 13, wherein the cable allows for the input module to be electrically linked to the control module at power-up.

16. The endoscopic system of claim 13, wherein the cable allows for the input module to be electronically linked to the control module when plugging the cable between the input module and the control module, and wherein the input module and the control module are already powered up.

17. The endoscopic system of claim 13, wherein the cable allows for controlling the power state of the input module from the control module and vice-versa through the third set of wires.

18. The endoscopic system of claim 13, wherein the cable allows a user to control one of the input module and control module from another of the input module and control module irrespective of the software used by the another of the input module and control module.

19. The endoscopic system of claim 13, wherein the software in the input module reprograms the software in the control module automatically upon connection of the input module to the control module and vice versa.

20. The endoscopic system of claim 13, wherein the input module has a first interface card and the control module has a second interface card, wherein the video data transmitted across the cable is processed by the first and second interface cards.

21. The endoscopic system of claim 13, wherein the input module converts the video data received by the camera head module into a data format recognizable by the control module, and wherein the input module transmits the reformatted video data to the control module.

22. An endoscopic system comprising:
a first input module adapted to be connectable with and to receive video data from a first camera head module;
a second input module adapted to be connectable with and to receive video data from a second camera head module;
a control module;
the first and second input modules adapted to be connectable with the control module and to convert the video data into a data format recognizable by the control module;
a first cable connecting the first input module to the control module, the first cable including a first set of wires, the first set of wires allowing for video data to be transmitted across the cable, a second set of wires, the second set of wires allowing for image control data to be transmitted across the cable, a third set of wires, the third set of wires allowing for power control data to be transmitted across the cable; and
a second cable connecting the second input module to the control module, the second cable including a first set of wires, the first set of wires allowing for video data to be transmitted across the cable, a second set of wires, the second set of wires allowing for image control data to be transmitted across the cable, a third set of wires, the third set of wires allowing for power control data to be transmitted across the cable,
wherein upon connection of the first input module to the control module via the cable, software automatically executes in the control module to transmit image control data through the second set of wires to determine if the software in the control module is compatible with the software in the first input module,
wherein, upon connection of the input module to the control module, the cable allows for image control data to be automatically transferred between the first input module and the control module through the second set of wires for software in the control module to program software files in the first input module, so that the first input module is compatible with the control module, and
wherein after the software files in the first input module are programmed, power is automatically cycled to the first input module.

23. The endoscopic system of claim 22, wherein upon connection of the second input module to the control module via the second cable, software executes in the control module to transmit image control data through the second set of wires of the second cable to determine if the software in the control module is compatible with the software in the second input module.

24. The endoscopic system of claim 22, further comprising an auxiliary input module.

25. The endoscopic system of claim 24, further comprising a third cable, the third cable connecting the auxiliary input module to the control module, the third cable including a first set of wires, the first set of wires allowing for video data to be transmitted across the cable, a second set of wires, the second set of wires allowing for control data to be transmitted across the cable, a third set of wires, the third set of wires allowing for power control data to be transmitted across the cable.

26. The endoscopic system of claim 25, wherein upon connection of the auxiliary input module to the control module via the third cable, software executes in the control module to transmit image control data through the second set of wires of the third cable to determine if the software in the control module is compatible with the software in the auxiliary input module.

27. The endoscopic system of claim 22, wherein the control module is linked to a PC or external network via an Ethernet link.

28. The endoscopic system of claim 25, further comprising a room camera and a PC, the room camera and the PC being linked to the auxiliary input module.

29. The endoscopic system of claim 22, wherein the first camera head module and the second camera head module transmit video data in different formats.

30. The endoscopic system of claim 29, wherein the first input module converts the video data received by the first camera head module into a data format recognizable by the control module, and wherein the second input module converts the video data received by the second camera head module into a data format recognizable by the control module.

31. A method for reprogramming modules in a modular endoscopic system in a medical operating room, the method comprising the steps of:
providing a control module;
providing an input module;
connecting the input module to a camera, the input module converting video data received from the camera into a data format recognizable by the control module; and
connecting the input module via a cable to the control module, such that upon connection of the input module to the control module via the cable, software in the control module automatically executes to transmit control data to determine if the software in the control module is compatible with software in the input module, and
such that upon connection of the control module to the input module, the cable allows for control data to be automatically transferred from the control module to the input module and vice-versa, and for software in the control module to reprogram software files in the input module, so that the input module is compatible with the control module,
wherein after the software files in either the control module or the input module are reprogrammed, at least one electrical connection automatically cycles power to the module whose software files have been reprogrammed.

* * * * *